US012746186B2

(12) United States Patent
Niwa et al.

(10) Patent No.: US 12,746,186 B2
(45) Date of Patent: Sep. 29, 2026

(54) DENTAL WORKPIECE AND METHOD FOR PRODUCING SAME

(71) Applicant: KURARAY NORITAKE DENTAL INC., Kurashiki (JP)

(72) Inventors: Takahiro Niwa, Aichi (JP); Kirihiro Nakano, Aichi (JP); Shinichiro Kato, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 8 days.

(21) Appl. No.: 18/870,497

(22) PCT Filed: Jun. 1, 2023

(86) PCT No.: PCT/JP2023/020517
§ 371 (c)(1),
(2) Date: Nov. 29, 2024

(87) PCT Pub. No.: WO2023/234400
PCT Pub. Date: Dec. 7, 2023

(65) Prior Publication Data

US 2025/0345247 A1 Nov. 13, 2025

(30) Foreign Application Priority Data

Jun. 1, 2022 (JP) ................................ 2022-089663

(51) Int. Cl.
*A61K 6/818* (2020.01)

(52) U.S. Cl.
CPC .................................... *A61K 6/818* (2020.01)

(58) Field of Classification Search
None
See application file for complete search history.

(56) References Cited

U.S. PATENT DOCUMENTS

| | | | |
|---|---|---|---|
| 9,573,850 | B2 | 2/2017 | Citti et al. |
| 2011/0212826 | A1 | 9/2011 | Cabodi et al. |

(Continued)

FOREIGN PATENT DOCUMENTS

| | | | |
|---|---|---|---|
| CN | 1489988 | A | 4/2004 |
| CN | 100473373 | C | 4/2009 |

(Continued)

OTHER PUBLICATIONS

International Search Report issued Aug. 8, 2023, in PCT/JP2023/020517 (with English translation), 5 pages.
Written Opinion of the International Searching Authority issued Aug. 8, 2023, in PCT/JP2023/020517 (with English translation), 6 pages.

(Continued)

*Primary Examiner* — Nicholas D Lucchesi
(74) *Attorney, Agent, or Firm* — Element IP, PLC

(57) ABSTRACT

The present invention provides a dental workpiece that exhibits excellent machinability in a sintered state while possessing suitable strength for dental use. The present invention relates to a dental workpiece that exhibits an erosion rate of 8.0 μm/g or more, or a product of erosion rate (μm/g)×average crystal grain size (μm) greater than or equal to 15 $\mu m^2/g$ when a spherical alumina slurry with an average particle diameter of 3.0 μm is projected in a micro slurry-jet erosion test, and that has a biaxial flexural strength of 300 MPa or more as measured in compliance with ISO 6872: 2015.

8 Claims, 1 Drawing Sheet

(56) References Cited

U.S. PATENT DOCUMENTS

| | | | | |
|---|---|---|---|---|
| 2013/0209951 A1* | 8/2013 | Piascik | .................... | A61C 7/14 427/2.27 |
| 2015/0183690 A1 | 7/2015 | Kim et al. | | |
| 2023/0014792 A1 | 1/2023 | Fukiage et al. | | |
| 2023/0052915 A1 | 2/2023 | Kato et al. | | |

FOREIGN PATENT DOCUMENTS

| | | | | | |
|---|---|---|---|---|---|
| CN | 111848157 A | * | 10/2020 | ........... | C04B 35/622 |
| CN | 116751054 A | * | 9/2023 | ............. | C04B 35/48 |
| JP | 2015127294 A | | 7/2015 | | |
| JP | 2019108289 A | | 7/2019 | | |
| JP | 2021091602 A | | 6/2021 | | |
| WO | WO-2021132644 A1 | | 7/2021 | | |

OTHER PUBLICATIONS

Iwai, Y., et al., “Evaluation and Analysis of Coating Strength by Micro Slurry-Jet Erosion (MSE) Test Method”, Surface Technology, 2017, vol. 68, No. 12. p. 702-706 (with partial machine translation).

Matsubara, T., “Strength Evaluation of Material Surface by MSE (Micro Slurry-jet Erosion) Test Method”, Powder Technology, 20 21, vol. 13, No. 1, pp. 40-47 (with partial machine translation).

Written Opposition filed Feb. 14, 2025, against the corresponding Japanese Patent No. 7535211, obtained on Mar. 10, 2025 (with machine English translation), 136 pages.

Extended European Search Report issued May 19, 2026, in corresponding European Patent Application No. 23816157.4, 8 pages.

Hui, H., et al., “Influence of Compaction Pressure and Pre-sintering Temperature on the Machinability of Zirconia Ceramic”, West China Journal of Stomatology, vol. 29, No. 5, Oct. 2011, pp. 534-536 (with machine English translation), 10 pages.

* cited by examiner

DENTAL WORKPIECE AND METHOD FOR PRODUCING SAME

TECHNICAL FIELD

The present invention relates to a dental workpiece and a method of production thereof. More specifically, the present invention relates to a dental workpiece that exhibits excellent machinability in a sintered state while having superior strength and translucency, and to a method for producing such a dental workpiece.

BACKGROUND ART

Ceramics made from metal oxides are used in a wide range of industrial applications. Notably, zirconia sintered bodies have found use in dental materials, such as dental prostheses, due to their high strength and aesthetic qualities.

Because of superior strength, zirconia sintered bodies hardly involve issues such as damage when used in dental materials such as prostheses. Zirconia sintered bodies also have high translucency and resistance to staining in the oral cavity, leading to their superior aesthetic qualities. However, once fully sintered, zirconia sintered bodies exhibit hardness that makes it nearly impossible to process with a dental processing machine. For example, machining a cubic zirconia sintered body into the desired tooth form for a patient results in substantial wear on metal processing tools and demands a considerable amount of time, even for producing just one dental prosthesis.

For these reasons, zirconia sintered bodies, when used in dental material applications, are typically processed into the shape of a desired dental prosthesis while in a more easily processable, semi-sintered state known as a pre-sintered body, rather than as a fully sintered body. The shaped pre-sintered body is then sintered into a sintered body in the required dental prosthesis shape. Afterward, minor adjustments are made to the sintered body to ensure that its shape as a dental prosthesis fits comfortably when placed in the patient's mouth at the dental clinic.

In recent years, CAD/CAM systems have been utilized to machine pre-sintered bodies into the required shape for dental prostheses, allowing customization to fit the patient's teeth at the treatment site. CAD/CAM-compatible pre-sintered bodies (mill blanks) are commonly used for this purpose.

As discussed above, when zirconia sintered bodies are used for dental material applications, major machining after sintering is avoided due to the unique challenges associated with sintering of zirconia. Instead, efforts are directed towards making only minor adjustments to the sintered body when it is placed in the patient's mouth at the dental clinic. In other words, the approach accommodates the gradual changes in physical properties due to zirconia sintering in dental material applications.

In dental treatment, taking into account the unique circumstances stemming from the physical properties of zirconia sintered bodies, the typical procedure involves a number of steps including: collecting data on the shape within the patient's oral cavity, such as dentition; machining a pre-sintered body (mill blank) into the desired dental prosthesis shape using a CAD/CAM system based on this data; sintering the pre-sintered body in the desired dental prosthesis shape to obtain a sintered body: and making minor adjustments to the sintered body to ensure that it comfortably fits when placed in the patient's mouth at the dental clinic.

This makes it challenging to complete all the steps in a single visit in dental treatment using dental prostheses made of zirconia sintered bodies. As a result, even for the treatment of a single tooth, patients usually need to make multiple trips to the dental clinic, and the entire treatment often takes more than a month to complete.

From the patient's standpoint, it is desirable to minimize the number of clinic visits to reduce the time before the new artificial tooth can be fitted after the treatment is started and to ease the burden of multiple visits. The need for shorter treatment times is growing each year.

If it is possible to perform extensive machining on zirconia sintered bodies in the sintered state, there is no need to machine a pre-sintered body and sinter it to produce a sintered body. Instead, the unprocessed sintered body can be machined into the desired dental prosthesis shape using a CAD/CAM system based on data collected in advance on the oral cavity shape of the patient. This sintered body can then be placed in the patient's mouth and minor adjustments can be made to complete the dental treatment in one day.

Although one-day dental treatments with dental prostheses are possible with non-zirconia materials such as lithium disilicate glass ceramic or feldspathic glass ceramic, accomplishing this with zirconia sintered bodies is highly challenging due to the unique challenges resulting from the physical properties of zirconia sintered bodies.

Given the high demand for zirconia for its strength and aesthetic qualities, and the increasing need for reducing treatment times, there have been proposed zirconia sintered bodies that exhibit superior machinability in the sintered state and can be processed into the desired dental prosthesis shape from prism- or disc-shaped mill blanks (for example, Patent Literatures 1 and 2).

For example, Patent Literature 1 discloses a processable zirconia as a sintered body formed by incorporating a tetragonal zirconia composite powder and a $TiO_2$ nanopowder, where the tetragonal zirconia composite powder contains 79.8 to 92 mol % $ZrO_2$ and 4.5 to 10.2 mol % $Y_2O_3$ along with 3.5 to 7.5 mol % $Nb_2O_5$ or 5.5 to 10.0 mol % $Ta_2O_5$, and the $TiO_2$ nanopowder is incorporated in a mass ratio of more than 0 mass % and 2.5 mass % or less relative to the zirconia composite powder. A method of production of this zirconia sintered body is also disclosed.

Patent Literature 2 discloses a machinable zirconia composition using raw materials that comprise 78 to 95 mol % $ZrO_2$ and 2.5 to 10 mol % $Y_2O_3$, along with 2 to 8 mol % $Nb_2O_5$ and/or 3 to 10 mol % $Ta_2O_5$, and in which the primary crystal phase of $ZrO_2$ is monoclinic. A method of production of this zirconia composition is also disclosed.

CITATION LIST

Patent Literature

Patent Literature 1: JP 2015-127294 A
Patent Literature 2: WO2021/132644

SUMMARY OF INVENTION

Technical Problem

The zirconia sintered bodies disclosed in Patent Literatures 1 and 2 are machinable even in their sintered form. However, these zirconia sintered bodies involve long processing times to cut out dental prostheses, and require further improvements in terms of reducing treatment times.

Furthermore, while the zirconia sintered bodies disclosed in Patent Literatures 1 and 2 are machinable, a continuous process with a single processing tool can produce only a small number of dental prostheses. Additionally, the tool wears out quickly, necessitating frequent replacements, which increases tool change times and reduces both productivity and cost-effectiveness.

Another issue is that reducing the hardness of the material to improve machinability results in decreased material strength.

It is an object of the present invention to provide a dental workpiece that exhibits excellent machinability in a sintered state while possessing strength suited for dental use.

Another object of the invention is to provide a dental workpiece that can be machined in a sintered state with short machining times while reducing wear on processing tools, increasing the number of dental prostheses that can be cut out in continuous processing with a single processing tool, leading to increased productivity and cost-effectiveness.

Solution to Problem

The present inventors conducted intensive studies to find a solution to the foregoing issues, and found that these issues can be solved when a dental workpiece with a biaxial flexural strength of 300 MPa or more exhibits an erosion rate of 8.0 μm/g or more, or a product of erosion rate (μm/g)× average crystal grain size (μm) greater than or equal to 15 $\mu m^2/g$ when a spherical alumina slurry with an average particle diameter of 3.0 μm is projected in a micro slurry-jet erosion test. This led to the completion of the present invention after further examinations.

Specifically, the present invention includes the following.

[1] A dental workpiece that exhibits an erosion rate of 6.5 μm/g or more, or a product of erosion rate (μm/g)× average crystal grain size (μm) greater than or equal to 15 $\mu m^2/g$ when a spherical alumina slurry with an average particle diameter of 3.0 μm is projected in a micro slurry-jet erosion test, and that has a biaxial flexural strength of 300 MPa or more as measured in compliance with ISO 6872:2015.

[2] The dental workpiece according to [1], which exhibits an erosion rate of 8.0 μm/g or more when a spherical alumina slurry with an average particle diameter of 3.0 μm is projected in a micro slurry-jet erosion test.

[3] The dental workpiece according to [1] or [2], which is a ceramic sintered body.

[4] The dental workpiece according to [3], wherein the ceramic sintered body is a sintered body containing zirconia.

[5] The dental workpiece according to any one of [1] to [4], which has an average crystal grain size of 0.05 to 15.0 μm.

[6] The dental workpiece according to any one of [1] to [5], which exhibits a product of erosion rate (μm/g)× average crystal grain size (μm) greater than or equal to 15 $\mu m^2/g$ when a spherical alumina slurry with an average particle diameter of 3.0 μm is projected in a micro slurry-jet erosion test.

[7] The dental workpiece according to [5], which has an average crystal grain size of 3.0 μm to 15.0 μm, and exhibits a product of erosion rate (μm/g)×average crystal grain size (μm) greater than or equal to 15 $\mu m^2/g$ when a spherical alumina slurry with an average particle diameter of 3.0 μm is projected in a micro slurry-jet erosion test.

[8] The dental workpiece according to [5], which has an average crystal grain size of 0.05 μm to 5.0 μm, and exhibits an erosion rate of 8.0 μm/g or more when a spherical alumina slurry with an average particle diameter of 3.0 μm is projected in a micro slurry-jet erosion test.

Advantageous Effects of Invention

According to the present invention, a dental workpiece can be provided that exhibits excellent machinability in a sintered state while possessing strength suited for dental use.

According to the present invention, a dental workpiece can be provided that possesses translucency suitable for dental use.

The present invention can also provide a dental workpiece that, when it is a sintered body containing zirconia or a sintered body containing alumina, can be machined in a sintered state with short machining times while reducing wear on processing tools, increasing the number of dental prostheses that can be cut out in continuous processing with a single processing tool (hereinafter, also referred to simply as “continuous processing”), leading to increased productivity and cost-effectiveness.

DESCRIPTION OF EMBODIMENTS

Figure 1:
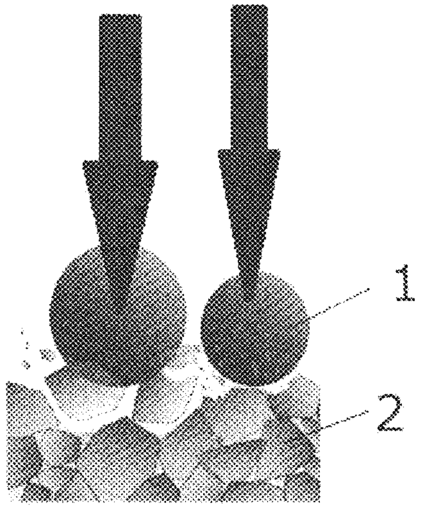
FIG. 1 is a schematic view representing how spherical alumina collides in the MSE test of the present invention.

A dental workpiece of the present invention exhibits an erosion rate of 6.5 μm/g or more, or a product of erosion rate (μm/g)×average crystal grain size (μm) greater than or equal to 15 $\mu m^2/g$ when a spherical alumina slurry with an average particle diameter of 3.0 μm is projected in a micro slurry-jet erosion (MSE: Micro Slurry-jet Erosion) test (hereinafter, also referred to as “MSE test”), and has a biaxial flexural strength of 300 MPa or more as measured in compliance with ISO 6872:2015.

Preferably, a dental workpiece of the present invention is a ceramic sintered body. Examples of the ceramic sintered body include sintered bodies containing zirconia, and sintered bodies containing alumina.

In the following, the term “processable zirconia composite sintered body” is also used to refer to zirconia-containing sintered bodies that exhibit excellent machinability in a sintered state.

A certain preferred embodiment is, for example, a dental workpiece that is a ceramic sintered body containing zirconia. A sintered body containing zirconia refers to a state where $ZrO_2$ particles (powder) are fully sintered (sintered state).

In this specification, the upper limits and lower limits of numeric ranges (for example, ranges of contents of components, ranges of proportions or values calculated from components, and ranges of physical properties) can be appropriately combined.

In this specification, machining encompasses both cutting and grinding. Machining may be a wet or dry process, without specific restrictions.

In view of achieving machinability in a sintered state while exhibiting superior strength for dental use, a dental workpiece of the present invention satisfies at least one of the following (i) and (ii) when a spherical alumina slurry with an average particle diameter 3.0 μm is projected in an MSE test:

(i) an erosion rate of 6.5 μm/g or more; and (ii) a product of erosion rate (μm/g)×average crystal grain size (μm) greater than or equal to 15 $\mu m^2/g$.

A dental workpiece of the present invention may satisfy both (i) and (ii).

In view of achieving machinability in a sintered state while exhibiting superior strength for dental use, a dental workpiece of the present invention in a certain preferred embodiment (hereinafter, also referred to as embodiment (A) exhibits an erosion rate of 6.5 μm/g or more, preferably 8.0 μm/g or more, more preferably 8.5 μm/g or more when a spherical alumina slurry with an average particle diameter of 3.0 μm is projected in an MSE test. In view of even superior machinability in a sintered state, the erosion rate is even more preferably 9.0 μm/g or more, particularly preferably 10.0 μm/g or more, most preferably 12.0 μm/g or more.

In embodiment (A), the upper limit of erosion rate is not particularly limited, as long as the present invention can exhibit its effects. However, the upper limit of erosion rate is preferably 100.0 μm/g or less, more preferably 60.0 μm/g or less, even more preferably 40.0 μm/g or less, particularly preferably 30.0 μm/g or less.

In embodiment (A), with the erosion rate falling within these ranges, it is believed that a dental workpiece of the present invention, when it is, for example, a ceramic sintered body (preferably, a sintered body containing zirconia), can reduce the strength of the interface (also referred to as "grain boundary" hereinbelow) of the constituent particles in the sintered body within a range suited for dental use. This can lead to superior machinability in a sintered state, shorter machining times, and reduced wear on processing tools, increasing the number of dental prostheses that can be cut in continuous processing.

While maintaining the erosion rate within the foregoing ranges can lead to superior machinability in a sintered state through reduced grain boundary strength, this can be achieved without compromising the strength suited for dental use, satisfying both strength and machinability in a sintered state.

The MSE testing method (hereinafter, also referred to as "localized slurry jet erosion method") is a procedure used to assess the mechanical properties of materials based on energy scales by employing a fine particles projection technique.

In the MSE testing method, the quantity of fine particles colliding under a constant collision velocity corresponds to the applied energy, and the resulting wear amount indicates the material's strength.

In the MSE testing method, a device is used that combines a unit for creating wear damage due to particle collisions, and a unit for measuring the shape of the projection marks (erosion marks). FIG. 1 is a schematic view representing how spherical alumina collides in the MSE testing method. FIG. 1 shows how spherical alumina 1, ejected from the projection nozzle, strikes the sintered body 2, causing abrasion in the sintered body 2. The shape measurement unit measures the projection marks (erosion marks) created by the projection of spherical alumina 1. FIG. 1 provides a partial enlarged view of spherical alumina 1, projected from the projection gun 42 equipped with the projection nozzle 50 depicted in FIG. 2, striking the sintered body 2, or sample W.

Figure 2:
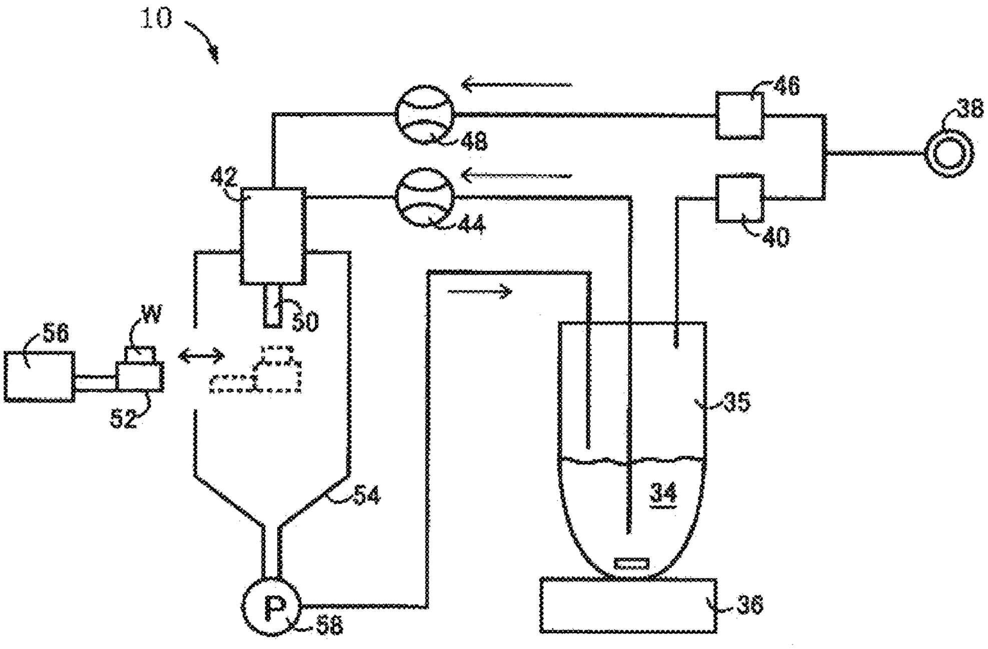
FIG. 2 is a schematic view representing an example of an MSE testing device used for the MSE test of the present invention.

An example of an MSE testing device includes a projection unit equipped with a projection gun and a projection nozzle; a shape measurement unit (for capturing the profile of projection marks); and a data processing unit. FIG. 2 represents one such example of an MSE testing device.

In the localized slurry jet erosion device 10 depicted in FIG. 2, the slurry 34 is contained in a slurry tank 35 and is stirred by an agitator 36.

A compressed air source 38 applies slurry pressure to the slurry tank 35 through a slurry pressure regulating valve 40, enabling the slurry 34 in slurry tank 35 to be supplied to the projection gun 42 via a slurry flow meter 44.

The compressed air source 38 also supplies air pressure to the projection gun 42 via an air pressure regulating valve 46 and an airflow meter 48.

The projection nozzle 50, situated at the bottom of the projection gun 42, is a nozzle with a projection cross-sectional area of 1.0 $mm^2$ (1 mm in length×1 mm in width), and is enclosed by a projection booth 54.

The projection gun 42 mixes the supplied slurry 34 with air, and locally ejects the mixture through the projection nozzle 50 at a distance of 4 mm toward a dental workpiece sample W secured to a fixture 52. This creates localized wear on the surface of the dental workpiece sample W, resulting in the formation of depressions.

The fixture 52, which secures the dental workpiece sample W, is transported in and out of the projection booth 54 by a table drive unit 56. The slurry 34 accumulated in the projection booth 54 is transferred back into the slurry tank 35 by a recovery pump 58.

The MSE testing device may be a known device (for example, the localized slurry jet erosion device MSR-A manufactured by Palmeso Co., Ltd.).

In the MSE test employed in this specification, a slurry with dispersed spherical alumina with an average particle diameter of 3.0 μm is projected onto the dental workpiece (sintered body). This process breaks down the grain boundaries, and the resulting depth of the eroded sintered body is used to calculate the erosion rate, using the following formula.

$$\text{Erosion rate } [\mu m/g] = \text{depth of wear } [\mu m] \div \text{mass of projected slurry } [g]$$

In this specification, the MSE test was conducted using the measurement conditions described in the EXAMPLES section below. The spherical alumina may be a commercially available product (for example, product number: MSE-BA-3-3, manufactured by Palmeso Co., Ltd.).

The average particle diameter of the spherical alumina slurry used in the MSE test can be measured by volume using, for example, a laser diffraction particle size distribution analyzer (SALD-2300, manufactured by Shimadzu Corporation) with a 0.2% sodium hexametaphosphate aqueous solution used as dispersion medium.

The following embodiment is described through the case where the dental workpiece of embodiment (A) is a sintered body containing zirconia. Because a dental workpiece of the present invention is not limited to sintered bodies containing zirconia, "sintered body containing zirconia" can be read as referring to "sintered body containing alumina", except where specified otherwise.

The sintered body containing zirconia is preferably one comprising $ZrO_2$, $HfO_2$, a stabilizer capable of preventing a phase transformation of zirconia, and $Nb_2O_5$ and/or $Ta_2O_5$, along with an optional Group I element.

The preferred embodiments described below are based on a zirconia-containing sintered body comprising $ZrO_2$, $HfO_2$, a stabilizer capable of preventing a phase transformation of zirconia (hereinafter, also referred to simply as "stabilizer"), and $Nb_2O_5$ and/or $Ta_2O_5$, along with an optional Group I element.

In the sintered body containing zirconia, the total content of $ZrO_2$ and $HfO_2$ is preferably 78 to 97.5 mol % in total 100 mol % of $ZrO_2$, $HfO_2$, the stabilizer, $Nb_2O_5$, and $Ta_2O_5$. In view of even superior translucency and strength, the total content of $ZrO_2$ and $HfO_2$ is more preferably 79 mol % or more and 96 mol % or less, even more preferably 80 mol % or more and 94 mol % or less, particularly preferably 81 mol % or more and 93 mol % or less.

In a sintered body containing alumina, the $Al_2O_3$ content in total 100 mol % of $Al_2O_3$, $Nb_2O_5$, and $Ta_2O_5$ may refer to the total content of $ZrO_2$ and $HfO_2$ in the sintered body containing zirconia. However, in certain preferred embodiments, the $Al_2O_3$ content is preferably 78 to 99 mol % in total 100 mol % of $Al_2O_3$, $Nb_2O_5$, and $Ta_2O_5$. In view of even superior translucency and strength, the $Al_2O_3$ content is more preferably 80 mol % or more and 98.8 mol % or less, even more preferably 82 mol % or more and 98.5 mol % or less, particularly preferably 83 mol % or more and 98.4 mol % or less.

The stabilizer may be absent in the sintered body containing alumina.

Examples of the stabilizer capable of preventing a phase transformation of zirconia include oxides such as calcium oxide (CaO), magnesium oxide (MgO), yttrium oxide ($Y_2O_3$), cerium oxide ($CeO_2$), scandium oxide ($Sc_2O_3$), lanthanum oxide ($La_2O_3$), erbium oxide ($Er_2O_3$), praseodymium oxide ($Pr_2O_3$, $Pr_6O_{11}$), samarium oxide ($Sm_2O_3$), europium oxide ($Eu_2O_3$), thulium oxide ($Tm_2O_3$), gallium oxide ($Ga_2O_3$), indium oxide ($In_2O_3$), and ytterbium oxide ($Yb_2O_3$). In view of enhancing the effectiveness of the present invention, particularly aesthetics, preferred are $Y_2O_3$ (yttria) and/or $CeO_2$. The stabilizer may be used alone, or two or more thereof may be used in combination.

In the sintered body containing zirconia, the content of the stabilizer capable of preventing a phase transformation of zirconia is preferably 1 to 12 mol %, more preferably 2 mol % or more and 10 mol % or less in total 100 mol % of $ZrO_2$, $HfO_2$, the stabilizer, $Nb_2O_5$, and $Ta_2O_5$. In view of even superior translucency and strength, the stabilizer content is even more preferably 3 mol % or more and 8 mol % or less, particularly preferably 3.5 mol % or more and 7.5 mol % or less.

A certain preferred embodiment is, for example, a sintered body containing zirconia in which the stabilizer capable of preventing a phase transformation of zirconia comprises $Y_2O_3$ and/or $CeO_2$, and the total content of $Y_2O_3$ and $CeO_2$ is 2 mol % or more and 10 mol % or less.

Another certain preferred embodiment is, for example, a sintered body containing zirconia in which the stabilizer capable of preventing a phase transformation of zirconia comprises $Y_2O_3$, and the $Y_2O_3$ content is 2 mol % or more and 10 mol % or less.

In any of the embodiments above, the content of $Y_2O_3$ and $CeO_2$ may be appropriately varied within the ranges specified in this specification. For example, in view of even superior translucency and strength, the total content of $Y_2O_3$ and $CeO_2$ may be 2.5 mol % or more and 10 mol % or less, or 3 mol % or more and 9 mol % or less.

It remains unclear why the sintered body containing zirconia allows for machining in the sintered state with its high machinability while exhibiting an erosion rate within the foregoing ranges and possessing strength and translucency suited for dental use. However, the following speculation has been made.

In the zirconia-containing sintered body comprising $ZrO_2$, $HfO_2$, a stabilizer capable of preventing a phase transformation of zirconia, and $Nb_2O_5$ and/or $Ta_2O_5$ along with Group I elements, the presence of Group I elements at the grain boundary of zirconia particles appears to reduce the grain boundary strength, facilitating particles to separate, thereby improving grindability. Presumably, this leads to an erosion rate within the foregoing ranges, resulting in improved machinability in the sintered state (particularly in continuous processing) while reducing a decrease in strength.

In a zirconia-containing sintered body comprising $Nb_2O_5$ and/or $Ta_2O_5$, $Nb_2O_5$ and/or $Ta_2O_5$ serve to coarsen the microstructure and reduce hardness, and, by acting integrally with Group I elements, improve machinability. Through this integrated action, $Nb_2O_5$ and/or $Ta_2O_5$ and Group I elements can provide excellent free-machinability while ensuring the strength needed as artificial teeth. This results in an erosion rate within the foregoing ranges, reducing the machining time of the sintered body and increasing the number of dental prostheses that can be produced in continuous processing with a single processing tool while reducing wear on processing tools. It is believed that this can resolve the specific challenges associated with the continuous processing of sintered bodies.

The Group I elements, when present at the grain boundary of zirconia particles, also appear to reduce the grain boundary strength, and facilitate particle separation and improve grindability by making adjustments such as increasing their content, even when the zirconia-containing sintered body does not comprise $Nb_2O_5$ and/or $Ta_2O_5$. As a result, the erosion rate can remain within the foregoing ranges, improving machinability in the sintered state (particularly in continuous processing) while reducing a decrease in strength.

In a zirconia-containing sintered body of the present invention, the Group I elements serve as an agent that imparts free-machinability in the manner described above, resulting in an erosion rate within the foregoing ranges, without causing significant reductions in strength and translucency.

The content of Group I elements contained in a zirconia-containing sintered body of the present invention (particularly, a sintered body containing $Nb_2O_5$ and/or $Ta_2O_5$) is preferably more than 0 mol % and 3 mol % or less. In view of providing even superior machinability in a sintered state and increasing the number of dental prostheses that can be produced in continuous processing with a single processing tool, the content of Group I elements is more preferably 0.05 mol % or more and 3 mol % or less. In view of particularly superior machinability in a sintered state and even shorter machining times, the content of Group I elements is even more preferably 0.06 mol % or more and 2.5 mol % or less, particularly preferably 0.07 mol % or more and 1.0 mol % or less, most preferably 0.08 mol % or more and 0.34 mol % or less.

These ranges are also applicable to the content of Group I elements in a sintered body containing alumina.

Another preferred embodiment is a zirconia-containing sintered body that does not comprise $Nb_2O_5$ and/or $Ta_2O_5$, and in which the content of Group I elements is 0.5 mol % or more and 6 mol % or less. In view of providing even superior machinability in a sintered state and increasing the number of dental prostheses that can be produced in continuous processing with a single processing tool, the content of Group I elements is more preferably 0.8 mol % or more and 5 mol % or less, even more preferably 1.0 mol % or more and 4.0 mol % or less, particularly preferably 1.2 mol % or more and 3.5 mol % or less, most preferably 1.5 mol % or more and 3.0 mol % or less.

Examples of the Group I elements include Li, Na, K, Rb, Cs, and Fr. In view of the ability to more greatly improve machinability in a sintered state, preferred are Li, Na, and K. The Group I elements may be used alone, or two or more thereof may be used in combination.

As described above, the Group I elements act integrally with $Nb_2O_5$ and/or $Ta_2O_5$, and these components do not compromise the effectiveness of the stabilizer.

Accordingly, the present invention can exhibit its effects without particularly restricting the choice of stabilizer.

In a zirconia-containing sintered body of the present invention, the total content of $Nb_2O_5$ and $Ta_2O_5$ is preferably 1 to 9 mol %, more preferably 1.5 mol % or more and 8.5 mol % or less in total 100 mol % of $ZrO_2$, $HfO_2$, the stabilizer, $Nb_2O_5$, and $Ta_2O_5$. In view of integrated action with Group I elements and even superior machinability in a sintered state, the total content of $Nb_2O_5$ and $Ta_2O_5$ is even more preferably 2.5 mol % or more and 8 mol % or less, particularly preferably 3 mol % or more and 7 mol % or less.

Sufficient machinability is more easily achievable in a sintered state when the total content of $Nb_2O_5$ and $Ta_2O_5$ is 1 mol % or more. When the total content of $Nb_2O_5$ and $Ta_2O_5$ is 9 mol % or less, it is easier to provide sufficient properties by reducing the occurrence of defects such as chipping in the resulting dental workpiece.

In an alumina-containing sintered body of the present invention, the total content of $Nb_2O_5$ and $Ta_2O_5$ is preferably 0.5 mol % or more and 9 mol % or less, more preferably 0.8 mol % or more and 8.5 mol % or less in total 100 mol % of $Al_2O_3$, $Nb_2O_5$, and $Ta_2O_5$. In view of integrated action with Group I elements and even superior machinability in a sintered state, the total content of $Nb_2O_5$ and $Ta_2O_5$ is even more preferably 1.0 mol % or more and 8 mol % or less, particularly preferably 1.5 mol % or more and 7 mol % or less.

Sufficient machinability is more easily achievable in a sintered state when the total content of $Nb_2O_5$ and $Ta_2O_5$ is 0.5 mol % or more. When the total content of $Nb_2O_5$ and $Ta_2O_5$ is 9 mol % or less, it is easier to provide sufficient properties by reducing the occurrence of defects such as chipping in the resulting dental workpiece.

In addition to serving to coarsen the microstructure and reduce hardness, and acting integrally with Group I elements to provide excellent free-machinability as noted above, $Nb_2O_5$ and $Ta_2O_5$ also interact with other components (for example, $TiO_2$, $Al_2O_3$) incorporated in the sintered body containing zirconia. This interaction, combined with the application of HIP, helps maximize the sintering density, providing natural tooth aesthetics.

In this specification, the content of each component in the dental workpiece can be calculated from the quantities of raw materials used.

The content of the components $ZrO_2$, $HfO_2$, stabilizer, $Nb_2O_5$, and $Ta_2O_5$ in the dental workpiece can be measured using a technique, for example, such as inductively coupled plasma (ICP) emission spectral analysis or X-ray fluorescence analysis.

The content (mol %) of Group I element refers to the proportion external to total 100 mol % of $ZrO_2$, $HfO_2$, the stabilizer, $Nb_2O_5$, and $Ta_2O_5$. Accordingly, the content of Group I element in the dental workpiece can be calculated by converting the quantity (mass) of the raw material added into mol %.

The content of zirconia enhancer (mass %) is the proportion external to total 100 mass % of $ZrO_2$, $HfO_2$, the stabilizer, $Nb_2O_5$, and $Ta_2O_5$. Accordingly, the content of zirconia enhancer in the dental workpiece can be calculated from the quantity (mass) of the raw material added.

The content of the components $ZrO_2$, $HfO_2$, stabilizer, $Nb_2O_5$, and $Ta_2O_5$ represents the proportion of each component in total 100 mol % of $ZrO_2$, $HfO_2$, stabilizer, $Nb_2O_5$, and $Ta_2O_5$, and the sum of $ZrO_2$, $HfO_2$, stabilizer, $Nb_2O_5$, and $Ta_2O_5$ does not exceed 100 mol %. For example, when the raw material composition contains $Nb_2O_5$ but does not contain $Ta_2O_5$, the content of the components $ZrO_2$, $HfO_2$, stabilizer, and $Nb_2O_5$ refers to the proportion of each component relative to total 100 mol % of $ZrO_2$, $HfO_2$, stabilizer, and $Nb_2O_5$.

In view of machinability, the ratio A/B is preferably 0.9 to 3, more preferably 0.95 to 2, where A is the content of stabilizer in mol %, and B is the total content of $Nb_2O_5$ and $Ta_2O_5$ in mol %. Even more preferably, the ratio A/B is 1 to 1.6 in view of enhancing the effectiveness of the integrated action between Group I elements and $Nb_2O_5$ and/or $Ta_2O_5$, improving free-machinability, and increasing the number of dental prostheses that can be produced in continuous processing with a single processing tool while reducing wear on processing tools.

A certain preferred embodiment (A-1) is, for example, a dental workpiece that exhibits an erosion rate of 8.0 μm/g or more when a spherical alumina slurry with an average particle diameter of 3.0 μm is projected in a micro slurry-jet erosion test, and a biaxial flexural strength of 300 MPa or more as measured in compliance with ISO 6872:2015, and that comprises $ZrO_2$, $HfO_2$, a stabilizer capable of preventing a phase transformation of zirconia, and $Nb_2O_5$ and/or $Ta_2O_5$,

- wherein the total content of $ZrO_2$ and $HfO_2$ is 78 to 97.5 mol %, the content of the stabilizer is 1 to 12 mol %, and the total content of $Nb_2O_5$ and $Ta_2O_5$ is 1 to 9 mol % in total 100 mol % of $ZrO_2$, $HfO_2$, the stabilizer, $Nb_2O_5$, and $Ta_2O_5$,
- the dental workpiece further comprises a Group I element,
- the stabilizer comprises $Y_2O_3$ and/or $CeO_2$,
- the content of the Group I element is more than 0 mol % and 3 mol % or less relative to total 100 mol % of $ZrO_2$, $HfO_2$, the stabilizer, $Nb_2O_5$, and $Ta_2O_5$, and
- the dental workpiece has a ratio A/B of 0.9 to 3, where A is the content of the stabilizer in mol %, and B is the total content of $Nb_2O_5$ and $Ta_2O_5$ in mol %.

A certain embodiment (A-2) of the present invention is, for example, a dental workpiece that further comprises a zirconia enhancer, in addition to $ZrO_2$, $HfO_2$, the stabilizer capable of preventing a phase transformation of zirconia, $Nb_2O_5$ and/or $Ta_2O_5$, and the Group I element.

The zirconia enhancer refers to a strength enhancing agent with the capability to enhance the strength of the sintered body through integrated action with Group I elements in a dental workpiece comprising $ZrO_2$, $HfO_2$, a stabilizer capable of preventing a phase transformation of zirconia, and $Nb_2O_5$ and/or $Ta_2O_5$.

In a dental workpiece comprising a zirconia enhancer, it is also possible to appropriately modify the total content of $ZrO_2$ and $HfO_2$, the type and content of stabilizer, the total content of $Nb_2O_5$ and $Ta_2O_5$, the type and content of Group I element, and the ratio A/B, as noted above.

In the dental workpiece containing a zirconia enhancer, the content of zirconia enhancer is preferably more than 0 mass % and 5.0 mass % or less relative to total 100 mass % of $ZrO_2$, $HfO_2$, a stabilizer capable of preventing a phase transformation of zirconia, $Nb_2O_5$, and $Ta_2O_5$. In view of achieving even greater strength through integrated action with Group I elements when combined with Group I elements, the content of zirconia enhancer is more preferably 0.01 mass % or more and 4.5 mass % or less, even more preferably 0.5 mass % or more and 4.0 mass % or less.

Examples of the zirconia enhancer include $TiO_2$ and $Al_2O_3$. The zirconia enhancer may be used alone, or two or more thereof may be used in combination.

Another certain preferred embodiment is, for example, a dental workpiece in which the zirconia enhancer in any one of the embodiments above comprises $TiO_2$, and the content of $TiO_2$ is 0.6 to 3.7 mass %.

A certain preferred embodiment is, for example, a dental workpiece that exhibits an erosion rate of 8.0 μm/g or more when a spherical alumina slurry with an average particle diameter of 3.0 μm is projected in a micro slurry-jet erosion test, and a biaxial flexural strength of 300 MPa or more as measured in compliance with ISO 6872:2015, and that comprises $ZrO_2$, $HfO_2$, a stabilizer capable of preventing a phase transformation of zirconia, and $Nb_2O_5$ and/or $Ta_2O_5$,

- wherein the total content of $ZrO_2$ and $HfO_2$ is 78 to 97.5 mol %, the content of the stabilizer is 1 to 12 mol %, and the total content of $Nb_2O_5$ and $Ta_2O_5$ is 1 to 9 mol % in total 100 mol % of $ZrO_2$, $HfO_2$, the stabilizer, $Nb_2O_5$, and $Ta_2O_5$,
- the dental workpiece further comprises a Group I element, the stabilizer comprises $Y_2O_3$ and/or $CeO_2$,
- the zirconia enhancer comprises $TiO_2$, and the content of $TiO_2$ is 0.6 to 3.7 mass %,
- the content of the Group I element is more than 0 mol % and 3 mol % or less relative to total 100 mol % of $ZrO_2$, $HfO_2$, the stabilizer, $Nb_2O_5$, and $Ta_2O_5$, and
- the dental workpiece has a ratio A/B of 0.9 to 3, where A is the content of the stabilizer in mol %, and B is the total content of $Nb_2O_5$ and $Ta_2O_5$ in mol %.

As described above, by keeping the erosion rate within the foregoing ranges, the dental workpiece, across different compositions, exhibits excellent machinability in a sintered state (particularly in continuous processing) while possessing strength suited for dental use.

A dental workpiece of the present invention has an average crystal grain size of preferably 0.05 to 15.0 μm. In view of even superior machinability, strength, and translucency in a sintered state, the average crystal grain size is more preferably 0.1 to 10.0 μm, even more preferably 0.3 to 7.0 μm, particularly preferably 0.5 to 5.0 μm. The method of measurement of average crystal grain size is as described in the EXAMPLES section below.

The average crystal grain size can be measured by adjusting the particle count in one SEM image field to about 50 or 100 particles, according to the method described in the EXAMPLES section below.

In view of providing superior machinability in a sintered state by efficiently utilizing the energy of alumina particle projection for breaking grain boundaries, it is preferable in embodiment (A) that the dental workpiece have an average crystal grain size of 0.05 μm to 5.0 μm. In view of even superior machinability, strength, and translucency in a sintered state, the average crystal grain size is more preferably 0.08 to 4.0 μm, even more preferably 0.1 to 3.5 μm, particularly preferably 0.3 to 3.0 μm.

In a certain preferred embodiment (hereinafter, also referred to as embodiment (B)), in view of achieving machinability in a sintered state while exhibiting superior strength for dental use, a dental workpiece of the present invention has a product of erosion rate (μm/g)×average crystal grain size (μm) greater than or equal to 15 $μm^2/g$ when a spherical alumina slurry with an average particle diameter of 3.0 μm is projected in an MSE test. In view of even superior machinability in a sintered state, the product of erosion rate (μm/g)×average crystal grain size (μm) is preferably 20 $μm^2/g$ or more, more preferably 23 $μm^2/g$ or more, even more preferably 25 $μm^2/g$ or more, particularly preferably 30 $μm^2/g$ or more.

In embodiment (B), the upper limit of erosion rate (μm/g)×average crystal grain size (μm) is not particularly limited, as long as the present invention can exhibit its effects. However, the upper limit of erosion rate (μm/g)×average crystal grain size (μm) is preferably 100 $μm^2/g$ or less, more preferably 80 $μm^2/g$ or less, even more preferably 65 $μm^2/g$ or less, particularly preferably 50 $μm^2/g$ or less.

Embodiment (B) does not differ from embodiment (A) with regard to the method and device used for the MSE test, and the measurement methods and conditions for erosion rate (μm/g) and average crystal grain size (μm).

In embodiment (B), the dental workpiece may have an average crystal grain size of 0.05 to 15.0 μm. However, in view of superior machinability in a sintered state, the average crystal grain size is preferably 3.0 μm to 15.0 μm, more preferably 4.0 to 15.0 μm, even more preferably 5.0 to 15.0 μm, particularly preferably 5.5 to 15.0 μm.

In embodiment (B), with the product of erosion rate (μm/g)×average crystal grain size (μm) falling within these ranges, it is believed that a dental workpiece of the present invention, when it is, for example, a ceramic sintered body (preferably, a sintered body containing zirconia), can reduce the strength of the interface (also referred to as "grain boundary" hereinbelow) of the constituent particles in the sintered body within a range suited for dental use by making adjustments such as significantly extending the firing time during the fabrication of the primary sintered body, despite the absence of Group I elements. This can lead to superior machinability in a sintered state, shorter machining times, and reduced wear on processing tools, increasing the number of dental prostheses that can be cut in continuous processing.

Concerning the product of erosion rate (μm/g)×average crystal grain size (μm), the denominator (g) in the erosion rate (μm/g) is intended to mean the mass of alumina slurry injected per unit time, and can be thought of as the work done on the sample because the alumina slurry, on average, is injected onto the sample at a constant rate. The numerator (μm) indicates the measured depth of the sample eroded by the alumina slurry as a result of injection.

That is, the product of average crystal grain size×erosion rate essentially represents the energy ($μm^2/W$) needed to erode a unit area ($μm^2$) per unit time.

It can therefore be said that this value has a correlation with machinability, and, in a dental workpiece of the present invention, machinability notably improves when the product of erosion rate (μm/g)×average crystal grain size (μm) is held within the foregoing ranges.

In a dental workpiece of the present invention, maintaining the product of erosion rate (μm/g)×average crystal grain size (μm) within the foregoing ranges can lead to superior machinability in a sintered state through reduced grain boundary strength, and this can be achieved without compromising the strength suited for dental use, satisfying both strength and machinability in a sintered state.

There is no particular restriction on erosion rate in embodiment (B). However, the erosion rate may be 8.0 μm/g or more, or less than 8.0 μm/g, or may be 6.5 μm/g or more, less than 6.5 μm/g, or 6.0 μm/g or less.

In embodiment (B), the erosion rate may overlap or exclude the erosion rate of embodiment (A), provided that the present invention can exhibit its effects.

In embodiment (B), when the erosion rate is 6.5 μm/g or more, it is possible to set an appropriate erosion rate from the preferred erosion rates specified in embodiment (A).

The following embodiment is described through the case where the dental workpiece of embodiment (B) is a sintered body containing zirconia.

Because a dental workpiece of the present invention is not limited to sintered bodies containing zirconia, "sintered body containing zirconia" can be read as referring to, for example, "sintered body containing alumina".

In a certain preferred embodiment (B-1), the zirconia-containing sintered body of embodiment (B) may be a zirconia-containing sintered body comprising $ZrO_2$, $HfO_2$, a stabilizer capable of preventing a phase transformation of zirconia, and $Nb_2O_5$ and/or $Ta_2O_5$, along with an optional Group I element.

Another certain preferred embodiment (B-2) is, for example, a zirconia-containing sintered body comprising $ZrO_2$, $HfO_2$, a stabilizer capable of preventing a phase transformation of zirconia, and $Nb_2O_5$ and/or $Ta_2O_5$, without Group I elements.

Embodiment (B), including embodiments (B-1) and (B-2), does not differ from embodiment (A) with regard to the total content of $ZrO_2$ and $HfO_2$, the type and content of the stabilizer capable of preventing a phase transformation of zirconia, the total content of $Nb_2O_5$ and $Ta_2O_5$, the type and content of Group I elements, the ratio A/B (A represents the stabilizer content in mol %, and B represents the total content of $Nb_2O_5$ and $Ta_2O_5$ in mol %), and the type and content of the zirconia enhancer.

In the processable zirconia composite sintered bodies of embodiment (A) and embodiment (B), higher densities result in fewer internal voids, improved translucency due to less light scattering, and enhanced strength. In view of this, the density of the processable zirconia composite sintered body is preferably 5.5 g/cm$^3$ or more, more preferably 5.7 g/cm$^3$ or more, even more preferably 5.9 g/cm$^3$ or more.

Particularly preferably, the processable zirconia composite sintered body is essentially void free.

The density of the composite sintered body can be calculated by dividing its mass by its volume ((mass of composite sintered body)/(volume of composite sintered body)).

In embodiments of sintered bodies containing zirconia, an example of a method for producing a dental workpiece of the present invention comprises the steps of:

- fabricating a molded body with a raw material composition that comprises $ZrO_2$, $HfO_2$, a stabilizer capable of preventing a phase transformation of zirconia, and $Nb_2O_5$ and/or $Ta_2O_5$, wherein the total content of $ZrO_2$ and $HfO_2$ is 78 to 97.5 mol %, the content of the stabilizer is 1 to 12 mol %, and the total content of $Nb_2O_5$ and $Ta_2O_5$ is 1 to 9 mol % in total 100 mol % of $ZrO_2$, $HfO_2$, the stabilizer, $Nb_2O_5$, and $Ta_2O_5$, and that optionally comprises a raw material compound of a Group I element; and
- sintering the molded body.

Unless stated otherwise, the conditions provided are applicable to all embodiments of the production method. For example, in embodiments where the sintered body contains alumina, the sintered body can be produced by modifying the production method for a dental workpiece that is a sintered body containing zirconia, for example, by changing components such as replacing $ZrO_2$ and $HfO_2$ with $Al_2O_3$, and excluding the stabilizer, and adjusting the content of each component within the ranges specified in this specification.

The raw material composition used for the production of the dental workpiece comprises $ZrO_2$, $HfO_2$, a stabilizer capable of preventing a phase transformation of zirconia, $Nb_2O_5$ and/or $Ta_2O_5$, and, optionally, a raw material compound of a Group I element. The raw material composition used for the production of the dental workpiece may be in a dry state, or in a liquid state containing liquid or contained in liquid. For example, the raw material composition may have a form of a powder, a granule or granulated material, a paste, or a slurry.

In a certain preferred embodiment, the raw material composition comprises a raw material compound of a Group I element to ensure that the dental workpiece contains a Group I element. Examples of the raw material compound of a Group I element include hydroxides and/or salts of Group I elements.

In another certain preferred embodiment, the raw material composition does not comprise a raw material compound of a Group I element.

When the raw material composition does not comprise a raw material compound of a Group I element, the product of erosion rate (μm/g)×average crystal grain size (μm) can be adjusted within the predetermined ranges by significantly extending the duration of sintering at the sintering temperature (highest sintering temperature) in sintering the molded body, which will be described later.

Examples of hydroxides of Group I elements include lithium hydroxide, sodium hydroxide, potassium hydroxide, rubidium hydroxide, cesium hydroxide, and francium hydroxide.

Examples of salts of Group I elements include carbonates and bicarbonates.

Examples of carbonates of Group I elements include lithium carbonate, sodium carbonate, potassium carbonate, rubidium carbonate, francium carbonate, and cesium carbonate.

Examples of bicarbonates of Group I elements include lithium bicarbonate, sodium bicarbonate, potassium bicarbonate, rubidium bicarbonate, francium bicarbonate, and cesium bicarbonate.

The hydroxides and salts of Group I elements may be used alone, or two or more thereof may be used in combination.

Commercially available zirconia powders can be used for $ZrO_2$ and $HfO_2$.

Examples of such commercially available products include zirconia powders manufactured by Tosoh Corporation under the trade names Zpex® ($Y_2O_3$ content: 3 mol %), Zpex® 4 ($Y_2O_3$ content: 4 mol %), Zpex® 4 Smile® ($Y_2O_3$ content: 5.5 mol %), TZ-3Y ($Y_2O_3$ content: 3 mol %), TZ-3YS ($Y_2O_3$ content: 3 mol %), TZ-4YS ($Y_2O_3$ content: 4 mol %), TZ-6Y ($Y_2O_3$ content: 6 mol %), TZ-6YS ($Y_2O_3$ content: 6 mol %), TZ-8YS ($Y_2O_3$ content: 8 mol %), TZ-10YS ($Y_2O_3$ content: 10 mol %), TZ-3Y-E ($Y_2O_3$ content: 3 mol %), TZ-3YS-E ($Y_2O_3$ content: 3 mol %), TZ-3YB-E ($Y_2O_3$ content: 3 mol %), TZ-3YSB-E ($Y_2O_3$ content: 3 mol %), TZ-3YB ($Y_2O_3$ content: 3 mol %), TZ-3YSB ($Y_2O_3$ content: 3 mol %), TZ-3Y20AB ($Y_2O_3$ content: 3 mol %), TZ-8YSB ($Y_2O_3$ content: 8 mol %), and TZ-0 ($Y_2O_3$ content: 0 mol %). These commercially available zirconia powders also contain $HfO_2$. It is also possible to use commercially available products additionally containing $Y_2O_3$. The raw material composition of the present invention may use zirconia powders in which $Y_2O_3$ is uniformly dispersed as a solid solution, as in the TZ series of the commercially available products listed above (those with "TZ" in the product names).

The method of production of zirconia powder is not particularly limited, and known methods may be employed, for example, such as the breakdown process, where coarse particles are pulverized into fine powder, or the building-up process, where synthesis occurs through nucleation and growth from atoms or ions.

The type of zirconia powder in the raw material composition is not particularly limited. It is possible to additionally incorporate stabilizer particles when the zirconia powder comprises $ZrO_2$ and $HfO_2$ but does not contain a stabilizer, or when increasing the content of stabilizer as needed. The stabilizer particles are not particularly limited, as long as the content of the stabilizer within the dental workpiece can be adjusted to the predetermined ranges mentioned above.

For example, the stabilizer particles may be commercially available products, and may be prepared by pulverizing a commercially available powder using a known pulverizing mixer (such as a ball mill).

In view of ease of obtaining the desired dental workpiece, a certain preferred embodiment is, for example, a method for producing a dental workpiece in which the stabilizer (preferably, $Y_2O_3$) comprises a stabilizer not dissolved in $ZrO_2$ and $HfO_2$ as a solid solution within the raw material composition. The presence of stabilizers not dissolved in zirconia as a solid solution can be verified, for example, through X-ray diffraction (XRD) patterns.

The presence of peaks derived from the stabilizer in an XRD pattern of the raw material composition or molded body means the presence of a stabilizer that is not dissolved in $ZrO_2$ and $HfO_2$ in the raw material composition or molded body.

A peak derived from the stabilizer is basically not observable in an XRD pattern when the stabilizer is fully dissolved in $ZrO_2$ and $HfO_2$ as a solid solution. It is, however, possible, depending on the crystal state or other conditions of the stabilizer, that the stabilizer is not dissolved in $ZrO_2$ and $HfO_2$ as a solid solution even when the XRD pattern does not show peaks for stabilizers.

The following describes situations where the stabilizer comprises a stabilizer not dissolved in $ZrO_2$ and $HfO_2$ as a solid solution, with yttria serving as an example of the stabilizer.

In the raw material composition or molded body of the present invention, the percentage presence $f_y$ of yttria not dissolved in $ZrO_2$ and $HfO_2$ as a solid solution (hereinafter, also referred to as "undissolved yttria") can be calculated using the following mathematical formula (1).

$$f_y = I_{29}/(I_{28} + I_{29} + I_{30}) \times 100$$

where $f_y$ represents the fraction (%) of undissolved yttria, $I_{28}$ represents the area intensity of a peak near 2θ=28°, where the main peak of the monoclinic crystal system appears in XRD measurement, $I_{29}$ represents the area intensity of a peak near 2θ=29°, where the main peak of yttria appears in XRD measurement, and $I_{30}$ represents the area intensity of a peak near 2θ=30°, where the main peak of the tetragonal or cubic crystal system appears in XRD measurement.

When additionally using stabilizers other than yttria, the formula can be applied to calculate the percentage presence of undissolved stabilizers other than yttria by substituting $I_{29}$ with the peaks of other stabilizers.

In view of considerations such as ease of obtaining the desired dental workpiece, the percentage presence $f_y$ of undissolved yttria is preferably higher than 0%, more preferably 1% or more, even more preferably 2% or more, particularly preferably 3% or more. The upper limit for the percentage presence $f_y$ of undissolved yttria may be, for example, 25% or less. Preferably, the upper limit of percentage presence $f_y$ of undissolved yttria depends on the yttria content in the raw material composition or molded body.

For example, the percentage presence $f_y$ of undissolved yttria falls within the following ranges when the yttria content in the raw material composition or molded body of the present invention is 3 mol % or more and 8 mol % or less. When the yttria content is 3 mol % or more and less than 4.5 mol %, $f_y$ may be 15% or less. When the yttria content is 4.5 mol % or more and less than 5.8 mol %, $f_y$ may be 20% or less. When the yttria content is 5.8 mol % or more and 8 mol % or less, $f_y$ may be 25% or less.

For example, when the yttria content is 3 mol % or more and less than 4.5 mol %, $f_y$ is preferably 2% or more, more preferably 3% or more, even more preferably 4% or more, particularly preferably 5% or more.

When the yttria content is 4.5 mol % or more and less than 5.8 mol %, $f_y$ is preferably 3% or more, more preferably 4% or more, even more preferably 5% or more, yet more preferably 6% or more, particularly preferably 7% or more.

When the yttria content is 5.8 mol % or more and 8 mol % or less, $f_y$ is preferably 4% or more, more preferably 5% or more, even more preferably 6% or more, yet more preferably 7% or more, particularly preferably 8% or more.

In the raw material composition or molded body of the present invention, it is not necessarily required for the stabilizer to be fully dissolved in $ZrO_2$ and $HfO_2$ as a solid solution. In the present invention, "stabilizer being dissolved as a solid solution" means that, for example, the elements (atoms) contained in the stabilizer are dissolved in $ZrO_2$ and $HfO_2$ as a solid solution.

There is no particular restriction on $Nb_2O_5$ and/or $Ta_2O_5$ incorporated in the raw material composition of the present invention, as long as the content of $Nb_2O_5$ and/or $Ta_2O_5$ within the dental workpiece can be adjusted in the predetermined ranges mentioned above. For example, commercially available products may be used for $Nb_2O_5$ and/or $Ta_2O_5$ without any particular restrictions. These may be used after pulverizing its powder using a known pulverizing mixer (such as a ball mill).

An example method of obtaining the raw material composition involves a process whereby the raw material composition is prepared by, for example, wet mixing each raw material of the raw material composition ($ZrO_2$, $HfO_2$, a stabilizer, $Nb_2O_5$ and/or $Ta_2O_5$, a raw material compound of a Group I element (for example, a hydroxide and/or salt of a Group I element), and, optionally, a zirconia enhancer) in a solvent containing water.

The method for wet mixing the raw materials in a solvent containing water is not particularly limited. For example, the raw materials may be formed into a slurry through wet pulverization and mixing using a known pulverizing mixer (such as a ball mill). The slurry can then be dried and granulated to produce a granular raw material composition.

In the wet mixing process, it is possible to additionally include additives such as binders, plasticizers, dispersants, emulsifiers, antifoaming agents, pH adjusters, and lubricants. The additives may be used alone, or two or more thereof may be used in combination.

The binder may be added to the pulverized slurry after the slurry is formed by adding a primary powder mixture of $ZrO_2$, $HfO_2$, $Y_2O_3$, $Nb_2O_5$ and/or $Ta_2O_5$, and a hydroxide and/or salt of a Group I element into water.

The binder is not particularly limited, and known binders may be used. Examples of the binders include polyvinyl alcohol binders, acrylic binders, wax binders (such as paraffin wax), methyl cellulose, carboxymethyl cellulose, polyvinyl butyral, polymethylmethacrylate, ethyl cellulose, polyethylene, polypropylene, ethylene-vinyl acetate copolymer, polystyrene, atactic polypropylene, and methacrylic resin.

Examples of the plasticizers include polyethylene glycol, glycerin, propylene glycol, and dibutyl phthalic acid.

Examples of the dispersants include ammonium polycarboxylates (such as triammonium citrate), ammonium polyacrylate, acrylic copolymer resin, acrylic acid ester copolymer, polyacrylic acid, bentonite, carboxymethyl cellulose, anionic surfactants (for example, polyoxyethylene alkyl ether phosphoric acid esters such as polyoxyethylene lauryl ether phosphoric acid ester), non-ionic surfactants, oleic glyceride, amine salt surfactants, oligosaccharide alcohols, and stearic acid.

Examples of the emulsifiers include alkyl ethers, phenyl ethers, sorbitan derivatives, and ammonium salts.

Examples of the antifoaming agents include alcohols, polyethers, silicone, and waxes.

Examples of the pH adjusters include ammonia, and ammonium salts (including ammonium hydroxides such as tetramethylammonium hydroxide).

Examples of the lubricants include polyoxyethylene alkylate ethers, and waxes.

The solvent used for wet mixing is not particularly limited, as long as it contains water. By using organic solvents, the solvent may be a mixed solvent of water and organic solvent. Alternatively, the solvent may be solely water. Examples of the organic solvents include ketone solvents such as acetone, and ethyl methyl ketone; and alcohol solvents such as ethanol, 1-propanol, 2-propanol, 2-methyl-2-propanol, glycerin, diglycerin, polyglycerin, propylene glycol, dipropylene glycol, polypropylene glycol, ethylene glycol, diethylene glycol, polyethylene glycol, polyethylene glycol monomethyl ether, 1,2-pentadiol, 1,2-hexanediol, and 1,2-octanediol.

The raw material composition used for the dental workpiece in the present invention may optionally comprise components other than $ZrO_2$, $Y_2O_3$, $Nb_2O_5$, $Ta_2O_5$, and the hydroxide and/or salt of a Group I element, the optionally incorporated zirconia enhancer, provided that the present invention can exhibit its effects. Examples of such additional components include colorants (pigments and composite pigments), fluorescent agents, and $SiO_2$. The additional components may be used alone, or two or more thereof may be used as a mixture.

Examples of the pigments include oxides of at least one element selected from the group consisting of V, Cr, Mn, Fe, Co, Ni, Zn, Y, Zr, Sn, Sb, Bi, Ce, Pr, Sm, Eu, Gd, Tb, and Er (specifically, such as NIO, and $Cr_2O_3$), preferably oxides of at least one element selected from the group consisting of V, Cr, Mn, Fe, Co, Ni, Zn, Y, Zr, Sn, Sb, Bi, Ce, Pr, Sm, Eu, Gd, and Tb, more preferably oxides of at least one element selected from the group consisting of V, Cr, Mn, Fe, Co, Ni, Zn, Y, Zr, Sn, Sb, Bi, Ce, Sm, Eu, Gd, and Tb. The pigments may exclude $Y_2O_3$ and $CeO_2$.

Examples of the composite pigments include $(Zr,V)O_2$, $Fe(Fe,Cr)_2O_4$, $(Ni,Co,Fe)(Fe,Cr)_2O_4{:}ZrSiO_4$, and $(Co,Zn)Al_2O_4$.

Examples of the fluorescent agents include $Y_2SiO_5{:}Ce$, $Y_2SiO_5{:}Tb$, $(Y,Gd,Eu)BO_3$, $Y_2O_3{:}Eu$, YAG:Ce, $ZnGa_2O_4{:}Zn$, and $BaMgAl_{10}O_{17}{:}Eu$.

Following its production, the raw material composition is molded to fabricate a molded body. The molding method is not particularly limited, and known molding methods can be used (for example, such as press molding).

When producing a zirconia molded body using a method that includes press molding the raw material composition, there are no specific limitations on the press molding method, and press molding may be achieved using known press molding machines. Specific examples of press molding methods include uniaxial pressing.

The molding pressure is appropriately set to an optimum value according to the desired size of molded body, open porosity, biaxial flexural strength, and the particle size of raw material powder. Typically, the molding pressure ranges from 5 MPa to 1,000 MPa. Increasing the molding pressure during molding in the method of production above allows for setting lower values for open porosity and increasing the density of the molded body by filling the voids more effectively in the molded body. To increase the density of the zirconia molded body obtained, cold isostatic pressing (CIP) may be applied after uniaxial pressing.

Following its production, the molded body is sintered.

The term "molded body" refers to a state that is neither a semi-sintered state (pre-sintered state) nor a sintered state. That is, the molded body is distinct from pre-sintered bodies and sintered bodies in that it has not been fired after molding.

The sintering temperature (highest sintering temperature) for obtaining the dental workpiece is, for example, preferably 1,300° C. or more, more preferably 1,350° C. or more, even more preferably 1,400° C. or more, yet more preferably 1,450° C. or more, particularly preferably 1,500° C. or more. The sintering temperature is, for example, preferably 1,680° C. or less, more preferably 1,650° C. or less, even more preferably 1,600° C. or less. Preferably, the method for producing a dental workpiece of the present invention involves firing the molded body at a highest sintering temperature of 1,300 to 1,680° C. The highest sintering temperature is preferably a temperature in the atmosphere.

In view of confining the erosion rate (μm/g) within the specified ranges according to embodiment (A), the hold time (retention time) at the highest sintering temperature is preferably 30 hours or less, more preferably 20 hours or less, even more preferably 10 hours or less, yet more preferably 5 hours or less, particularly preferably 3 hours or less, most preferably 2 hours or less, depending on the temperature, when the molded body is obtained using a raw material composition containing a raw material compound of a Group I element, and comprises a raw material compound of a Group I element. The hold time may be 25 minutes or less, 20 minutes or less, or 15 minutes or less. The hold time is preferably 1 minute or more, more preferably 5 minutes or more, even more preferably 10 minutes or more. A production method of the present invention enables the fabrication of a dental workpiece having superior flexural strength, translucency, and machinability in a manner that depends on the content of the stabilizer. The sintering time can be reduced, as long as the present invention can exhibit its effects. Shortening the sintering time can improve production efficiency and reduce energy costs.

Concerning embodiment (B), in view of adjusting the product of erosion rate (μm/g)×average crystal grain size (μm) within the predetermined ranges, the hold time (retention time) at the highest sintering temperature may be 41 hours or more, 45 hours or more, or 50 hours or more when the molded body does not contain a raw material compound of a Group I element. The hold time may be 200 hours or less, 150 hours or less, or 120 hours or less.

In the method for producing a dental workpiece of the present invention, the rate of temperature increase in sintering the molded body is not particularly limited, and is preferably 0.1° C./min or more, more preferably 0.2° C./min or more, even more preferably 0.5° C./min or more. The rate of temperature increase is preferably 50° C./min or less, more preferably 30° C./min or less, even more preferably 20° C./min or less. Productivity improves when the rate of temperature increase is at or above these lower limits.

A common dental zirconia furnace can be used for the sintering process of the molded body. The dental zirconia furnace may be a commercially available product. Examples of commercially available products include Noritake KATANA® F-1, F-1N, F-2 (SK Medical Electronics Co., Ltd.).

Preferably, the sintering process for the molded body includes a hot isostatic pressing (HIP) process, aside from sintering at the highest sintering temperature. The HIP process can further improve the translucency and strength of the dental workpiece.

In the following, the term "primary sintered body" is used to refer to sintered bodies obtained through sintering at the highest sintering temperature, whereas "HIP sintered body" is used to refer to sintered bodies after a HIP process.

Known hot isostatic pressing (HIP) devices can be used for HIP process.

The temperature for HIP process is not particularly limited. However, for advantages such as obtaining a high-strength and dense dental workpiece, the HIP temperature is preferably 1,200° C. or more, more preferably 1,300° C. or more, even more preferably 1,400° C. or more. The HIP temperature is preferably 1,700° C. or less, more preferably 1,650° C. or less, even more preferably 1,600° C. or less.

In the method for producing a dental workpiece of the present invention, the HIP pressure in the HIP process of the primary sintered body is not particularly limited. However, for advantages such as obtaining a high-strength and dense sintered body, the HIP pressure is preferably 100 MPa or more, more preferably 125 MPa or more, even more preferably 130 MPa or more. The upper limit of HIP pressure is not particularly limited, and may be, for example, 400 MPa or less, 300 MPa or less, or 200 MPa or less.

In the method for producing a dental workpiece of the present invention, the rate of temperature increase in the HIP process of the primary sintered body is not particularly limited, and is preferably 0.1° C./min or more, more preferably 0.2° C./min or more, even more preferably 0.5° C./min or more. The rate of temperature increase is preferably 50° C./min or less, more preferably 30° C./min or less, even more preferably 20° C./min or less. Productivity improves when the rate of temperature increase is at or above these lower limits.

In the method for producing a dental workpiece of the present invention, the duration of HIP in the HIP process of the primary sintered body is not particularly limited. However, for advantages such as obtaining a high-strength and dense dental workpiece, the duration of the HIP process is preferably 5 minutes or more, more preferably 10 minutes or more, even more preferably 30 minutes or more. The duration of the HIP process is preferably 10 hours or less, more preferably 6 hours or less, even more preferably 3 hours or less.

In the method for producing a dental workpiece of the present invention, the pressure medium in the HIP process of the primary sintered body is not particularly limited. However, in view of a low impact on zirconia, the pressure medium may be at least one selected from the group consisting of oxygen, oxygen with 3% hydrogen, air, and various inert gases (for example, nitrogen, argon).

When conducting HIP processing of the primary sintered body in an oxygen-mixed gas atmosphere, the oxygen concentration may be, for example, more than 0% and 20% or less, though it is not particularly limited.

When using an oxygen-mixed gas, at least one inert gas (for example, such as nitrogen or argon) may be selected as a gas other than oxygen.

In a method for producing a dental workpiece of the present invention, the HIP process may result in blackening due to oxygen deficiency when the process is carried out in a reducing atmosphere such as by using an inert gas. In order to prevent such blackening, it is preferable to include a heat treatment step (or tempering as it is also called hereinbelow), performed at 1,650° C. or less in either the atmosphere or an excess oxygen atmosphere, after the HIP process. In view of the efficiency of heat treatment, the heat treatment step is carried out preferably in an excess oxygen atmosphere. Here, excess oxygen atmosphere means an atmosphere where the oxygen concentration exceeds that of the atmosphere. The excess oxygen atmosphere is not particularly limited, as long as the oxygen concentration is higher than 21% and 100% or less, and can be appropriately selected within this range. For example, the oxygen concentration may be 100%.

A dental workpiece of the present invention may be a primary sintered body, a HIP sintered body, or a tempered sintered body with no particular restriction, provided that the present invention can exhibit its effects.

A certain preferred embodiment is, for example, a dental workpiece that has been tempered.

The heat treatment temperature in the atmosphere or an excess oxygen atmosphere may be appropriately varied according the aesthetics of the dental workpiece (for example, the shade of dental prostheses).

In a certain preferred embodiment, in view of the aesthetics of the dental workpiece, the heat treatment temperature in the atmosphere or an excess oxygen atmosphere is preferably 1,650° C. or less, more preferably 1,600° C. or less, even more preferably 1,550° C. or less.

In another preferred embodiment, in view of the aesthetics of the dental workpiece, the heat treatment temperature in the atmosphere or an excess oxygen atmosphere is preferably 1,400° C. or less, more preferably 1,300° C. or less, even more preferably 1,200° C. or less.

In either embodiment, the heat treatment temperature is preferably 500° C. or more, more preferably 600° C. or more, even more preferably 700° C. or more.

A common dental zirconia furnace can be used for the tempering process. The dental zirconia furnace may be a commercially available product. Examples of commercially available products include Noritake KATANA® F-1, F-1N, F-2 (SK Medical Electronics Co., Ltd.).

A dental workpiece of the present invention exhibits excellent machinability despite being a sintered body. It is accordingly not necessary to machine it as a mill blank of a pre-sintered body in a semi-sintered state before sintering into a sintered body.

Nonetheless, the dental workpiece can be produced using a method whereby a molded body obtained from the raw material composition is pre-sintered to form a semi-sintered-state pre-sintered body, and this pre-sintered body, unprocessed, is machined before sintering it to form a sintered body.

When the dental workpiece is a sintered body containing zirconia, another certain embodiment is, for example, a method for producing a dental workpiece that comprises the steps of fabricating a molded body using the raw material composition, pre-sintering the molded body to form a zirconia pre-sintered body (pre-sintering step), and sintering the zirconia pre-sintered body.

In order to ensure block formation, the firing temperature (pre-sintering temperature) in the pre-sintering step is, for example, preferably 800° C. or more, more preferably 900° C. or more, even more preferably 950° C. or more.

The pre-sintering temperature is, for example, preferably 1,200° C. or less, more preferably 1,150° C. or less, even more preferably 1,100° C. or less. The preferred range of pre-sintering temperatures is, for example, 800° C. to 1,200° C. It is believed that, at these pre-sintering temperatures, no significant progression of the formation of the solid solution of the stabilizer occurs in the pre-sintering step.

A zirconia pre-sintered body of the present invention refers to a state where $ZrO_2$ particles have formed necks between particles but the $ZrO_2$ particles (powder) have not been fully sintered (semi-sintered state).

The zirconia pre-sintered body has a density of preferably 2.7 g/cm$^3$ or more. The zirconia pre-sintered body has a density of preferably 4.0 g/cm$^3$ or less, more preferably 3.8 g/cm$^3$ or less, even more preferably 3.6 g/cm$^3$ or less. Processing becomes easier when the density falls within these ranges. The density of the pre-sintered body can be calculated, for example, as the mass-to-volume ratio of the pre-sintered body ((mass of pre-sintered body)/(volume of pre-sintered body)).

The zirconia pre-sintered body has a three-point flexural strength of preferably 15 to 70 MPa, more preferably 18 to 60 MPa, even more preferably 20 to 50 MPa.

The flexural strength can be measured in compliance with ISO 6872:2015 except for the specimen size, using a specimen measuring 5 mm in thickness, 10 mm in width, and 50 mm in length. For surface finishing, the specimen surfaces, including chamfered surfaces (45° chamfers at the corners of specimen), are finished longitudinally with #600 sandpaper. The specimen is disposed in such an orientation that its widest face is perpendicular to the vertical direction (loading direction). In the flexure test, measurements are made at a span of 30 mm with a crosshead speed of 1.0 mm/min.

The sintering step for the zirconia pre-sintered body can be conducted using the same method and conditions (such as temperature and pressure) used to sinter the molded body. Accordingly, in embodiments of the production method using zirconia pre-sintered bodies, the term “molded body” can be read as referring to “pre-sintered body”.

A dental workpiece of the present invention excels in strength. A dental workpiece of the present invention has a biaxial flexural strength of preferably 300 MPa or more, more preferably 350 MPa or more, even more preferably 400 MPa or more, yet more preferably 450 MPa or more, particularly preferably 500 MPa or more. A dental workpiece of the present invention, with its biaxial flexural strength falling in these ranges, can reduce defects, for example, such as fracture in the oral cavity, when used as a dental prosthesis. The upper limit of biaxial flexural strength is not particularly limited, and may be, for example, 1,200 MPa or less, or 1,000 MPa or less.

The biaxial flexural strength of the dental workpiece can be measured in compliance with ISO 6872:2015.

It is preferable that a dental workpiece of the present invention have high translucency. The translucency can be assessed using ΔL*. Specifically, a dental workpiece of the present invention has a translucency of preferably 10 or more, more preferably 12 or more, even more preferably 13 or more, particularly preferably 14 or more in terms of ΔL* for a diameter of 15 mm and a thickness of 1.2 mm. A dental workpiece with high translucency can be obtained with ΔL* falling within these ranges.

Here, ΔL* means the difference between the lightness (first L* value) against a white background and the lightness (second L* value) against a black background in the same sample. Specifically, ΔL* means the difference between the L* value against a white back ground (JIS Z 8781-4:2013 Color Measurements—Part 4: CIE 1976 L*a*b* color space) and the L* value against a black background. The white background means the white part of the hiding-power test paper described in JIS K 5600-4-1:1999, Part 4, Section 1, and the black background means the black part of the hiding-power test paper.

The upper limit of ΔL* is not particularly limited, and may be, for example, 25 or less. In view of aesthetics, ΔL* may be 20 or less.

A spectrophotometer can be used to measure ΔL* for a dental workpiece with a diameter of 15 mm and a thickness of 1.2 mm. For example, the dental colorimeter Crystaleye CE100-CE/JP with a 7-band LED illuminant and analysis software Crystaleye (manufactured by Olympus Corporation) may be used for measurement.

Examples of dental prostheses produced using a dental workpiece of the present invention include crown restorations such as inlays, onlays, veneers, crowns, core-integrated crowns, and bridges, as well as abutment teeth, dental posts, dentures, denture bases, and implant parts (fixtures, abutments). Preferably, for example, a commercially available dental CAD/CAM system is used for machining. Examples of such CAD/CAM systems include the CEREC system manufactured by Dentsply Sirona, and the KATANA® system manufactured by Kuraray Noritake Dental Inc.

A dental workpiece of the present invention can also be used in applications other than dental use, and is particularly suited for zirconia parts that require irregular or complex shapes and strength.

A dental workpiece of the present invention can be directly processed as a sintered body, instead of employing existing production methods (such as injection molding, CIP, casting, and 3D printing). This can be cost-effective, for example, when a desired zirconia part is obtained in short time periods. For parts that are complex in shape and difficult to produce with traditional methods, this technique eliminates the need for mechanical fitting of multiple parts, allowing for the production of zirconia parts with maintained high strength.

Furthermore, because the sintered body is directly processable, the sintering process can be eliminated when precise dimensions are needed, eliminating uneven shrinkage during firing, leading to high-precision zirconia parts. A dental workpiece of the present invention is also applicable to methods of manufacture in applications, specifically, such as in jewelry goods, engine parts and interior components of mobility vehicles such as aircraft and automobiles, display panel frames, construction members, electrical appliance components, components of household goods, and toy parts.

The zirconia parts can also be fitted with different materials to create composite components.

The present invention encompasses embodiments combining all or part of the foregoing features, provided that the present invention can exhibit its effects with such combinations made in various forms within the technical idea of the present invention.

EXAMPLES

The present invention is described below in greater detail through Examples. It is to be noted, however, that the present invention is in no way limited by the following Examples, and various modifications may be made by a person with ordinary skill in the art within the technical idea of the present invention. In the following Examples and Comparative Example, average particle diameter refers to average primary particle diameter, and can be determined using a laser diffraction scattering method. Specifically, the average particle diameter can be measured by volume using a laser diffraction particle size distribution analyzer (SALD-2300, manufactured by Shimadzu Corporation) with a 0.2% sodium hexametaphosphate aqueous solution used as dispersion medium.

Examples 1 to 8 and Comparative Example 1

The measurement samples for Examples and Comparative Example were prepared by fabricating a granular raw material composition, a molded body, and a sintered body (the fabrication of a primary sintered body, as well as HIP processing and tempering) through these processes.

[Fabrication of Granular Raw Material Composition]

To fabricate a granular raw material composition for each Example and Comparative Example, a mixture was prepared by combining commercially available powders of $ZrO_2$, $Al_2O_3$, $Y_2O_3$, $Nb_2O_5$, and $TiO_2$, along with a hydroxide or carbonate of a Group I element, according to the formulations specified in Tables 1 and 2. Subsequently, water was added to prepare a slurry, and the slurry was pulverized wet with a ball mill until it had an average particle diameter of 0.13 μm or less. After adding a binder to the pulverized slurry, the slurry was dried with a spray dryer to obtain a granular raw material composition (hereinafter, also referred to simply as "raw material composition"). This raw material composition was used to produce a molded body, as detailed below. Here, the average particle diameter is a measured value determined by volume using a laser diffraction particle size distribution analyzer (SALD-2300, manufactured by Shimadzu Corporation) with a 0.2% sodium hexametaphosphate aqueous solution used as dispersion medium.

[Fabrication of Molded Body]

For each Example and Comparative Example, pellet-shaped molded bodies and block-shaped molded bodies were produced in preparation for the fabrication of sintered body samples for both translucency and strength evaluation and processability evaluation, as follows.

A cylindrical mold with a diameter of 19 mm was used to create pellet-shaped molded bodies. The raw material composition was placed in the mold to ensure that sintering produces a dental workpiece with a thickness of 1.2 mm.

Subsequently, the raw material composition was molded under a surface pressure of 200 MPa to obtain a pellet-shaped molded body, using a uniaxial press molding machine.

For block-shaped molded bodies, the raw material composition was placed in a mold with inside dimensions of 19 mm×18 mm, ensuring that sintering produces a dental workpiece with a height of 14.5 mm.

Subsequently, the raw material composition was molded under a surface pressure of 200 MPa to obtain a block-shaped molded body, using a uniaxial press molding machine.

[Fabrication of Primary Sintered Body]

The pellet-shaped and block-shaped molded bodies were held for 2 hours in the atmosphere at the highest sintering temperatures specified in Tables 1 and 2, using the Noritake KATANA® F-1 furnace manufactured by SK Medical Electronics Co., Ltd. This resulted in zirconia- or alumina-containing sintered body (primary sintered body) samples in both pellet and block shapes.

In the following, the primary sintered body of Example 6 was evaluated for its properties as a dental workpiece, without HIP processing or tempering.

[Fabrication of HIP Sintered Body]

The pellet-shaped and block-shaped zirconia- or alumina-containing sintered bodies (primary sintered bodies) were held for 2 hours at 150 MPa and the HIP temperatures specified in Tables 1 and 2, using the HIP device $O_2$-Dr.HIP manufactured by Kobe Steel, Ltd. This resulted in zirconia- or alumina-containing sintered body (HIP sintered body) samples in both pellet and block shapes.

[Fabrication of Dental Workpiece (Tempered Sintered Body)]

The pellet-shaped and block-shaped zirconia- or alumina-containing sintered bodies (HIP sintered bodies) were held at 700° C. for 60 hours using the Noritake KATANA® F-1 furnace (manufactured by SK Medical Electronics Co., Ltd.) to prepare dental workpiece (tempered sintered body) samples in both pellet and block shapes.

The pellet-shaped samples had a diameter of 15 mm and a thickness of 1.2 mm. The block-shaped samples measured 15.7 mm in width, 16.5 mm in length, and 14.5 mm in height.

The content of each component in the sintered bodies presented in Tables 1 and 2 was calculated from the quantities of the raw materials used.

The content (mol %) of Group I elements in Tables 1 and 2 refers to the proportion external to total 100 mol % of $ZrO_2$, $HfO_2$, the stabilizer, $Nb_2O_5$, and $Ta_2O_5$.

The content (mol %) of $ZrO_2$, $HfO_2$, the stabilizer, $Nb_2O_5$, and $Ta_2O_5$ in Tables 1 and 2 refers to the content of each component in total 100 mol % of $ZrO_2$, $HfO_2$, the stabilizer, $Nb_2O_5$, and $Ta_2O_5$. For $ZrO_2$ and $HfO_2$, the content is presented as the total content of $ZrO_2$ and $HfO_2$.

The content (mass %) of $TiO_2$ in Tables 1 and 2 refers to the proportion external to total 100 mass % of $ZrO_2$, $HfO_2$, the stabilizer, $Nb_2O_5$, and $Ta_2O_5$.

A/B in Tables 1 and 2 represents the ratio of A to B, where A is the $Y_2O_3$ content in mol %, and B is the total content of $Nb_2O_5$ and $Ta_2O_5$ in mol %.

The dental workpiece obtained in each Example and Comparative Example was evaluated for its properties using the methods below. The results are presented in Tables 1 and 2.

[MSE Test]

A sample (15.7 mm wide×16.5 mm long×3.0 mm high) prepared from the processable zirconia composite sintered body of each Example and Comparative Example was evaluated using a localized slurry jet erosion device (Model MSR-A, manufactured by Palmeso Co., Ltd.).

For evaluation, a spherical alumina slurry was prepared by mixing spherical alumina (product number: MSE-BA-3-3, manufactured by Palmeso Co., Ltd.) of 3.0 μm average particle diameter with water at 3 volume %, and this spherical alumina slurry was used in the localized slurry jet erosion method. The spherical alumina slurry was used immediately after being prepared.

The projection pressure was adjusted by projecting the spherical alumina slurry onto a standard specimen (product number: HRC45, manufactured by Palmeso Co., Ltd.) to attain a reference value (erosion rate: 1.00 μm/g±5%).

The evaluation was carried out under the conditions set by selecting an impact mode with an air pressure of 0.335 MPa, a slurry pressure of 0.317 MPa, an airflow rate of 10.8 L/min, and a slurry flow rate of 125 L/min, all directed to the projection nozzle.

The projection force for this impact mode was verified by achieving an erosion rate of 24.0±5% μm/g on a standard specimen made of acrylic resin.

[Measurement of Wear Depth and Calculation of Erosion Rate]

The wear depth (erosion depth) of the sample was measured by injecting the spherical alumina slurry containing spherical alumina particles, using the localized slurry jet erosion method. For measurement, three points were randomly selected on each sample, and the sample was measured at each measurement point under the conditions below.

From the resulting profile, the maximum value D (μm) of the wear depth was measured at each measurement point. Using the predetermined relationship set for the spherical alumina slurry containing spherical alumina particles, the amount of projected particles (g) on the sample was then calculated based on the flow rate of the slurry supplied to the projection nozzle 50. Subsequently, the spherical particle-induced wear rate (spherical particle-induced erosion rate) (μm/g) according to the localized slurry jet erosion method with the spherical alumina slurry containing spherical alumina particles was calculated by dividing the average maximum value D (μm) of the sample by the amount of projected particles (g). The average erosion rate from the three measurement points is presented in Tables 1 and 2.

(Measurement Conditions)

Equipment: stylus-type measurement device (PU-EU1) manufactured by Kosaka Laboratory Ltd.
Probe load: 100 μN
Magnification: 10,000
Measured length: 4 mm
Measurement speed: 0.2 mm/sec

[Translucency Evaluation of Dental Workpiece]

The pellet-shaped dental workpiece (tempered sintered body) samples (approximately 15 mm in diameter×1.2 mm thickness) of each Example and Comparative Example were directly used to evaluate translucency, as follows (n=3). The dental colorimeter Crystaleye (7-band LED illuminant) manufactured by Olympus Corporation was used as the measurement device. First, a white background (underlay) was arranged for the sample (the opposite side of the sample from the measurement device is white), and the sample was measured for L* value according to L*a*b*color system (JIS Z 8781-4:2013 Color Measurements—Part 4: CIE 1976 L*a*b* color space). This was recorded as a first L* value. Thereafter, the same sample used for the measurement of first L* value was measured for L* value against a black background (underlay) according to L*a*b*color system (the opposite side of the sample from the measurement device is black). This was recorded as a second L* value.

In the present invention, the difference between the first and second L* values (the second L* value is subtracted from the first L* value) represents translucency, denoted as ΔL*. Higher ΔL* values indicate higher translucency, whereas lower ΔL* values indicate lower translucency. A hiding-power test paper used for measurement involving paints, as specified in JIS K 5600-4-1:1999, can be used for the black and white backgrounds (underlays) in the chromaticity measurement. The average ΔL* value for each sample is presented in Tables 1 and 2.

In embodiments requiring translucency, a ΔL* value of 10 or more was considered acceptable.

[Strength Evaluation of Dental Workpiece]

The pellet-shaped dental workpiece (tempered sintered body) samples of each Example and Comparative Example were directly used to measure biaxial flexural strength. The measurement was conducted using a universal testing machine AGS-X (manufactured by Shimadzu Corporation) with the crosshead speed set at 1.0 mm/min, following ISO6872:2015 (n=5). The measurement results are presented as average values in Tables 1 and 2. A strength of 300 MPa or more was considered acceptable.

[Measurement Method for Average Crystal Grain Size of Sintered Body]

Surface images were captured for the pellet-shaped dental workpiece (tempered sintered body) of each Example and Comparative Example, using a scanning electron microscope (VE-9800 manufactured by Keyence under this trade name). The average crystal grain size was calculated by image analysis after indicating grain boundaries on individual crystal grains in the image.

For the measurement of average crystal grain size, the captured SEM image was binarized with image analysis software (Image-Pro Plus manufactured by Hakuto Co., Ltd. under this trade name), and particles were recognized from the field (region) by adjusting the brightness range to provide clear grain boundaries. The crystal grain size from Image-Pro Plus is the average of the measurements of the length of a line segment connecting the contour line and passing through the center of gravity determined from the contour line of the crystal grain, conducted at 2-degree intervals with the center of gravity as the central point. The measurement of crystal grain size was conducted for all particles not extending beyond the edges of the SEM photographic image (3 fields) of each Example and Comparative Example. The average of the measured crystal grain sizes was then determined as the average crystal grain size (number-based) of the sintered body.

Note that particles not extending beyond the edges of the image are particles excluding those with contour lines extending beyond the screen of the SEM photographic image (particles with their contour lines interrupted by the boundary lines at the top, bottom, left, and right). To select the crystal grain size of all particles not extending beyond the edges of the image, the option in Image-Pro Plus was used that excludes all particles lying on the boundary lines.

[Processability Evaluation of Dental Workpiece]

For each Example and Comparative Example, thirty samples of block-shaped dental workpieces (tempered sintered bodies) were prepared, each with a metal jig attached to a surface approximately 15.7 mm in width and 14.5 mm in height. These samples were then processed into the shape of a typical anterior tooth crown using the CEREC system MC-XL manufactured by Dentsply Sirona. The software inLab® CAM version 20.0.1.203841 was used as a processing program, and the following parameters were selected: Manufacture: IVOCLAR VIVADENT, Material name: IPS e.max CAD, Production Method: Grinding, Block size: C16. For processing tools, Step Bur 12 and Cylinder Pointed Bur 12S were used.

[Processing Time]

The processing times presented in Tables 1 and 2 represent the duration needed to complete the processing of the first sample with a new processing tool, following the conditions outlined in the foregoing section [Processability Evaluation of Dental Workpiece].

If errors occurred during processing due to the processing load or some other factor, and the CEREC system MC-XL stopped working during processing, the process was resumed after replacing the tool with a new one. This procedure was repeated until one sample was fully processed, and the time required for this process was recorded as the processing time.

[Unit Count]

The unit count presented in Tables 1 and 2 represents the number of samples that were processed into the shape of an anterior tooth crown without having to replace the processing tool even once during the processing conducted with a new set of processing tools under the conditions outlined in the foregoing section [Processability Evaluation of Dental Workpiece]. Testing involved at a maximum of 30 samples. If all thirty samples were successfully processed with a single processing tool, no further tests were conducted, and the result was recorded as "30 or more" in all such instances.

If errors occurred during processing due to the processing load or some other factor, and the MC-XL stopped working before finishing the first sample, the process was resumed after replacing the tool with a new one. This procedure was repeated until one sample was fully processed, and the reciprocal of the number of tools used was recorded as a unit count. For example, "0.2" in Comparative Example 1 in Table 2 indicates that five processing tools were used to process one sample into the shape of an anterior tooth crown.

TABLE 1

| | Raw materials: $ZrO_2$, stabilizer ($Y_2O_3$), $Al_2O_3$, $Nb_2O_5$ or $Ta_2O_5$ | Raw materials: Raw material compound of Group I element | Raw materials: Optional component | Production conditions: Primary firing condition | Production conditions: HIP processing temperature [° C.] | Dental workpiece, Component content, Unit [mol %]: (1) $ZrO_2$ and $HfO_2$ | (2) $Y_2O_3$ (A) | $Al_2O_3$ | (3) $Nb_2O_5$ (B) | (4) $Ta_2O_5$ (B) | (1) to (4) in total | Group I element [mol %] | Optional component ($TiO_2$) [mass %] |
|---|---|---|---|---|---|---|---|---|---|---|---|---|---|
| Ex. 1 | $ZrO_2$, $Y_2O_3$, $Nb_2O_5$ | NaOH | $TiO_2$ | 1550° C. × 2 hours | 1450 | 90.30 | 5.30 | — | 4.40 | 0.00 | 100.00 | 0.18 | 2.73 |
| Ex. 2 | $ZrO_2$, $Y_2O_3$, $Nb_2O_5$ | NaOH | $TiO_2$ | 1550° C. × 2 hours | 1450 | 90.30 | 5.30 | — | 4.40 | 0.00 | 100.00 | 0.10 | 2.73 |
| Ex. 3 | $ZrO_2$, $Y_2O_3$, $Nb_2O_5$ | NaOH | $TiO_2$ | 1550° C. × 2 hours | 1450 | 90.30 | 5.30 | — | 4.40 | 0.00 | 100.00 | 0.05 | 2.73 |
| Ex. 4 | $ZrO_2$, $Y_2O_3$, $Nb_2O_5$ | None | $TiO_2$ | 1550° C. × 50 hours | 1450 | 90.30 | 5.30 | — | 4.40 | 0.00 | 100.00 | 0.00 | 2.73 |
| Ex. 5 | $ZrO_2$, $Y_2O_3$, $Nb_2O_5$ | None | $TiO_2$ | 1550° C. × 80 hours | 1450 | 90.30 | 5.30 | — | 4.40 | 0.00 | 100.00 | 0.00 | 2.73 |
| Ex. 6 | $ZrO_2$, $Y_2O_3$, | KOH | — | 1550° C. × 2 hours | — | 94.50 | 5.50 | — | 0.00 | 0.00 | 100.00 | 2.00 | 0.00 |
| Ex. 7 | $ZrO_2$, $Y_2O_3$, | KOH | — | 1550° C. × 2 hours | 1450 | 94.50 | 5.50 | — | 0.00 | 0.00 | 100.00 | 2.00 | 0.00 |
| Ex. 8 | $Al_2O_3$, $Nb_2O_5$ | $Na_2CO_3$ | — | 1450° C. × 2 hours | 1400 | 0.00 | 0.00 | 98.30 | 1.70 | 0.00 | 100.00 | 0.10 | 1.60 |

| | Raw materials: $ZrO_2$, stabilizer ($Y_2O_3$), $Al_2O_3$, $Nb_2O_5$ or $Ta_2O_5$ | Raw materials: Raw material compound of Group I element | Raw materials: Optional component | Production conditions: Primary firing condition | Production conditions: HIP processing temperature [° C.] | Dental workpiece: A/B | Average crystal grain size [μm] | Property values, Machinability: Processing time | Machinability: Unit count | Translucency ΔL* | Biaxial flexural strength [MPa] | Erosion rate [μm/g] | Average crystal grain size × erosion rate [$μm^2$/g] |
|---|---|---|---|---|---|---|---|---|---|---|---|---|---|
| Ex. 1 | $ZrO_2$, $Y_2O_3$, $Nb_2O_5$ | NaOH | $TiO_2$ | 1550° C. × 2 hours | 1450 | 1.2 | 2.7 | 19 m 35 s | 30 or more | 15.4 | 610 | 14.4 | 38.9 |
| Ex. 2 | $ZrO_2$, $Y_2O_3$, $Nb_2O_5$ | NaOH | $TiO_2$ | 1550° C. × 2 hours | 1450 | 1.2 | 2.8 | 25 m 50 s | 15 | 15.3 | 615 | 11.1 | 31.1 |
| Ex. 3 | $ZrO_2$, $Y_2O_3$, $Nb_2O_5$ | NaOH | $TiO_2$ | 1550° C. × 2 hours | 1450 | 1.2 | 2.3 | 45 m 16 s | 2 | 15.5 | 604 | 9.3 | 21.4 |
| Ex. 4 | $ZrO_2$, $Y_2O_3$, $Nb_2O_5$ | None | $TiO_2$ | 1550° C. × 50 hours | 1450 | 1.2 | 7.0 | 51 m 30 s | 2 | 15.3 | 520 | 3.5 | 24.5 |

TABLE 1-continued

| | | | | | | | | | | | | | |
|---|---|---|---|---|---|---|---|---|---|---|---|---|---|
| Ex. 5 | $ZrO_2$, $Y_2O_3$, $Nb_2O_5$ | None | $TiO_2$ | 1550° C. × 80 hours | 1450 | 1.2 | 9.4 | 42 m 5 s | 2 | 15.8 | 490 | 2.6 | 24.4 |
| Ex. 6 | $ZrO_2$, $Y_2O_3$, | KOH | — | 1550° C. × 2 hours | — | — | 1.7 | 26 m 05 s | 5 | 2.1 | 410 | 8.2 | 13.9 |
| Ex. 7 | $ZrO_2$, $Y_2O_3$, | KOH | — | 1550° C. × 2 hours | 1450 | — | 1.7 | 26 m 13 s | 5 | 15.3 | 480 | 8.1 | 13.8 |
| Ex. 8 | $Al_2O_3$, $Nb_2O_5$ | $Na_2CO_3$ | — | 1450° C. × 2 hours | 1400 | — | 8.5 | 17 m 12 s | 30 or more | 1.8 | 315 | 7.6 | 64.6 |

TABLE 2

| | Raw materials | | | Production conditions | | Dental workpiece: Component content | | | | | | |
|---|---|---|---|---|---|---|---|---|---|---|---|---|
| | | | | | | Unit [mol %] | | | | | | Optional |
| | $ZrO_2$, stabilizer ($Y_2O_3$), $Nb_2O_5$ or $Ta_2O_5$ | Raw material compound of Group I element | Optional component | Primary firing condition | HIP processing temperature [° C.] | (1) $ZrO_2$ and $HfO_2$ | (2) $Y_2O_3$ (A) | (3) $Nb_2O_5$ (B) | (4) $Ta_2O_5$ (B) | (1) to (4) in total | Group I element [mol %] | component ($TiO_2$) [mass %] |
| Com. Ex. 1 | $ZrO_2$, $Y_2O_3$, $Nb_2O_5$ | None | $TiO_2$ | 1550 × 2 hours | 1450 | 90.30 | 5.30 | 4.40 | 0.00 | 100.00 | 0.00 | 2.73 |

| | Raw materials | | | Production conditions | | | Dental workpiece: Property values | | | | | | |
|---|---|---|---|---|---|---|---|---|---|---|---|---|---|
| | | | | | | | | Machinability | | | | | |
| | $ZrO_2$, stabilizer ($Y_2O_3$), $Nb_2O_5$ or $Ta_2O_5$ | Raw material compound of Group I element | Optional component | Primary firing condition | HIP processing temperature [° C.] | A/B | Average crystal grain size [μm] | Processing time | Unit count | Translucency ΔL* | Biaxial flexural strength [MPa] | Erosion rate [μm/g] | Average crystal grain size × erosion rate [$μm^2$/g] |
| Com. Ex. 1 | $ZrO_2$, $Y_2O_3$, $Nb_2O_5$ | None | $TiO_2$ | 1550 × 2 hours | 1450 | 1.2 | 2.0 | 98 m | 0.2 | 15.2 | 603 | 6.1 | 12.2 |

These results confirmed that the dental workpieces of the present invention demonstrate excellent machinability in a sintered state while possessing strength and translucency suited for dental use.

In Examples 1 to 3, it was possible to reduce wear on processing tools, increasing the number of dental prostheses that can be continuously produced with a single processing tool compared to related art.

The dental workpieces of the present invention were also shown to exhibit excellent machinability in a sintered state while possessing strength and translucency suited for dental use, even in embodiments requiring high translucency.

In contrast, Comparative Example 1, which corresponds to Patent Literature 1 and where the erosion rate falls outside of the predetermined ranges, failed to achieve sufficient reduction in processing time.

INDUSTRIAL APPLICABILITY

A dental workpiece of the present invention exhibits excellent machinability while possessing suitable strength and translucency. A dental workpiece of the present invention is particularly useful as dental materials intended for dental treatment, such as dental prostheses.

REFERENCE SIGNS LIST

10: Localized slurry jet erosion device
34: Slurry
35: Slurry tank
36: Agitator
38: Compressed air source
40: Slurry pressure regulating valve
42: Projection gun
44: Slurry flow meter
46: Air pressure regulating valve
48: Airflow meter
50: Projection nozzle
52: Fixture
54: Projection booth
56: Table drive unit
58: Recovery pump

The invention claimed is:

1. A dental workpiece that exhibits an erosion rate of 6.5 μm/g or more, or a product of erosion rate (μm/g)×average crystal grain size (μm) greater than or equal to 15 $μm^2$/g when a spherical alumina slurry with an average particle diameter of 3.0 μm is projected at the dental workpiece in a micro slurry-jet erosion test, and that has a biaxial flexural strength of 300 MPa or more as measured in compliance with ISO 6872:2015.

2. The dental workpiece according to claim 1, which exhibits an erosion rate of 8.0 μm/g or more when a spherical alumina slurry with an average particle diameter of 3.0 μm is projected at the dental workpiece in a micro slurry-jet erosion test.

3. The dental workpiece according to claim 1, which is a ceramic sintered body.

4. The dental workpiece according to claim 3, wherein the ceramic sintered body is a sintered body containing zirconia.

5. The dental workpiece according to claim 1, which has an average crystal grain size of 0.05 to 15.0 μm.

6. The dental workpiece according to claim 5, which has an average crystal grain size of 3.0 μm to 15.0 μm, and exhibits a product of erosion rate (μm/g)×average crystal grain size (μm) greater than or equal to 15 $\mu m^2/g$ when a spherical alumina slurry with an average particle diameter of 3.0 μm is projected at the dental workpiece in a micro slurry-jet erosion test.

7. The dental workpiece according to claim 5, which has an average crystal grain size of 0.05 μm to 5.0 μm, and exhibits an erosion rate of 8.0 μm/g or more when a spherical alumina slurry with an average particle diameter of 3.0 μm is projected at the dental workpiece in a micro slurry-jet erosion test.

8. The dental workpiece according to claim 1, which exhibits a product of erosion rate (μm/g)×average crystal grain size (μm) greater than or equal to 15 $\mu m^2/g$ when a spherical alumina slurry with an average particle diameter of 3.0 μm is projected at the dental workpiece in a micro slurry-jet erosion test.

* * * * *